US009937345B2

(12) United States Patent
Knisely et al.

(10) Patent No.: US 9,937,345 B2
(45) Date of Patent: Apr. 10, 2018

(54) COCHLEAR IMPLANT

(71) Applicant: The Regents of the University of Michigan, Ann Arbor, MI (US)

(72) Inventors: Katherine Elizabeth Knisely, Ann Arbor, MI (US); Karl Grosh, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 356 days.

(21) Appl. No.: 14/624,391

(22) Filed: Feb. 17, 2015

(65) Prior Publication Data

US 2015/0231394 A1 Aug. 20, 2015

Related U.S. Application Data

(60) Provisional application No. 61/940,709, filed on Feb. 17, 2014.

(51) Int. Cl.
*A61N 1/36* (2006.01)
*A61N 1/378* (2006.01)
*A61N 1/05* (2006.01)

(52) U.S. Cl.
CPC ....... *A61N 1/36032* (2013.01); *A61N 1/3785* (2013.01); *A61N 1/0541* (2013.01)

(58) Field of Classification Search
CPC . A61N 1/0541; A61N 1/36032; A61N 1/3785
See application file for complete search history.

(56) References Cited

U.S. PATENT DOCUMENTS 5,344,387 A 9/1994 Lupin
2015/0012059 A1 1/2015 Kim et al.

FOREIGN PATENT DOCUMENTS

WO 1991005523 A1 5/1991

OTHER PUBLICATIONS

Piazza, Gianluca et al., "Piezoelectric Aluminum Nitride Thin Films for Microelectromechanical Systems", Materials Research Society Bulletin, vol. 37, Nov. 2012, pp. 1051-1061.
G. Iriarte, et al., "Influence of Deposition Parameters on the Stress of Magnetron Sputter-Deposited AlN Thin Films on Si(100) Substrates," J. Mater. Res. 18(2):423-432 (2003).
G. F. Iriarte, J. Rodriguez, and F. Calle, "Synthesis of c-axis oriented AlN thin films on different substrates: A review," Materials Research Bulletin 45:1039-1045 (2010).
A. Johnson, "An active thin-film cochlear electrode array with monolithic backing and curl," PhD Thesis, The University of Michigan, 178 pages (2011).

(Continued)

*Primary Examiner* — Amanda Patton
(74) *Attorney, Agent, or Firm* — Howard & Howard Attorneys PLLC

(57) ABSTRACT

A device for implantation into a scalia tympani of a cochlea is disclosed. The device comprises blocks and compliant elements interconnecting the blocks with one of the compliant elements disposed between each pair of adjacent blocks. The compliant elements impart flexibility to the device in a plane of curvature of the cochlea and impart stiffness to the device out of the plane of curvature of the cochlea. The device further comprises piezoelectric elements with at least one of the elements disposed the blocks. Each piezoelectric element comprises at least one piezoelectric sensing unit and at least one electrode for transmitting the electrical signal to the auditory nerve. The device further comprises communication lines for transmitting an electrical signal through the device with one of the communication lines disposed between each pair of blocks and parallel to the compliant element.

15 Claims, 9 Drawing Sheets

(56) References Cited

OTHER PUBLICATIONS

A. Johnson and K. Wise, "A self-curling monolithically-backed active high-density cochlear electrode array," Proceedings of the IEEE International Conference on Micro Electra Mechanical Systems (MEMS) 2012:914-917 (2012).
Y. Jung, et al., "Development of a Multi-Channel Piezoelecric Acoustic Sensor Based on an Artificial Basilar Membrane," Sensors 14:117-128 (2014).
M. Kimber, R. Lonergan, and S. V. Garimella, "Experimental study of aerodynamic damping in arrays of vibrating cantilevers," Journal of Fluid Structures 25:1334-1347 (2009).
K. Knisely and K. Grosh, "Effect of AC target power on AlN film quality," J. Vac. Sci. Technol. A 32(5)/051504 (2014).
A. Kral and A. Sharma, "Developmental neuroplasticity after cochlear implantation," Trends in Neurosciences, 35(2):111-122 (2012).
M. Krommer and H. Irschik, "On the influence of the electric field on free transverse vibrations of smart beams," J. Smart Mater. Struct. 8:401-410 (1999).
H. Kroncke, et al., "Determination of the Temperature Dependent Thermal Expansion Coefficients of Bulk AlN By HRXRD," Acta Physica Polonica A 114(5):1193-1200 (2008).
K. Kusaka, et al., "Effect of the input power on crystal orientation and residual stress in AlN film deposited by dc sputtering," Vacuum 59:806-813 (2000).
R. Littrell, "High Performance Piezoelectric MEMS Microphones," Ph.D. Thesis, University of Michigan, Ann Arbor, 112 pages (2010).
R. Littrell and K. Grosh, "Modeling and Characterization of Cantilever-Based MEMS Piezoelectric Sensors and Actuators," Journal of Microelectromechanical Systems 21(2):406-413 (2012).
H. Loebl, et al., "Piezoelectric thin AlN films for bulk acoustic wave (BAW) resonators," Materials Chemistry and Physics 79:143-146 (2003).
R. Mahameed, et al., "Dual-beam actuation of piezoelectric AlN RF MEMS switches monolithically integrated with AlN contour-mode resonators," J. Micromech. Microeng. 18:1-11 (2008).
F. Martin, P. Muralt, and M. A. Dubois, "Process optimization for the sputter deposition of molybdenum thin films as electrode for AlN thin films," J. Vac. Sci. Technol. A 24(4):946-952 (2006).
F. Martin, et al., "Thickness dependence of the properties of highly c-axis textured AlN thin films," J. Vac. Sci. Technol. A 22(2):361-365 (2004).
M. Martin and B. Houston, "Frequency Response of Cylindrical Resonators in a Viscous Fluid," Journal of Vibration and Acoustics 133/031009-1-6 (2011).
J. Meyer, et al., "High Density Interconnects and Flexible Hybrid Assemblies for Active Biomedical Implants," IEEE Transactions on Advanced Packaging 24(3):366-374 (2001).
J. R. Mileham, et al., "Wet chemical etching of AlN," Appl. Phys. Lett. 67(8):1119-1121 (1995).
J. M. Miller, et al., "Neurotropins can enhance spiral ganglion cell survival after inner hair cell loss," Int. J. Devl. Neuroscience 15(4/5):631-643 (1997).
S. Mishin and M. Gutkin, "Effect of substrate material and electrode surface preparation on stress and piezoelectric properties of aluminum nitride," IEEE Transactions on Ultrasonics, Ferroelectrics, and Frequency Control, 3 pages (2011).
S. Mishin, et al., "Sputtered AlN Thin Films on Si and Electrodes for MEMS Resonators: Relationship Between Surface Quality Microstructure and Film Properties," 2003 IEEE Ultrasonics Symposium, pp. 2028-2032 (2003).
M. Moreira, et al., "Electrical characterization and morphological properties of AlN films prepared by dc reactive magnetron sputtering," Microelectronic Engineering 88:802-806 (2011).
C. C. Morton and W. Nance, "Newborn Hearing Screening—A Silent Revolution," The New England Journal of Medicine, 354(20):2151-2164 (2006).

N. Mukherjee and R. Roseman, "Considerations in the development of a piezoelectric transducer cochlear implant," Mat. Res. Soc. Symp. Proc. 604:79-84 (2000).
B. A. Murphy, "A Biocompatibility Study of Aluminum Nitride Packaging for Cortical Implants," Ph.D. Thesis, Wayne State University, 204 pages (2008).
T. Naik, E. Longmire, and S. Mantell, "Dynamic response of a cantilever in liquid near a solid wall," Sensors and Actuators A 102:240-254 (2003).
E. Olson, "Intracochlear pressure measurements related to cochlear tuning," J. Acoust. Soc. Am. 110(1):349-367 (2001).
A. Pandey and R. Pratap, "Effect of flexural modes on squeeze film damping in MEMS cantilever resonators," J. Micromech. Microeng. 17:2475-2484 (2007).
G. Piazza and A. Pisano, "Two-port stacked piezoelectric aluminum nitride contour-mode resonant MEMS," Sensors and Actuators A 136:638-645 (2007).
J. L. Pinyon, et al., "Close-Field Electroporation Gene Delivery Using the Cochlear Implant Electrode Array Enhances the Bionic Ear," Science Translational Medicine 6(233):233ra54 (2014).
H. L. Rehm, et al., "Understanding the Genetics of Deafness: A Guide for Patients and Families," Harvard Medical School Center for Hereditary Deafness, Cambridge, MA, 29 pages (2003).
W. Rhode, "Observations of the Vibrations of the Basilar Membrane in Squirrel Monkeys using the Mossbauer Technique," J. Acoust. Soc. Am. 49(4):1218-1231, 1971.
D. Riss, et al., "Envelope Versus Fine Structure Speech Coding Strategy: A Crossover Strategy," Otology & Neurotology 32:1094-1101 (2011).
K. Roach, "Electrochemical Models for Electrode Behavior in Retinal Prostheses," Ph.D. Thesis, Massachusetts Institute of Technology, 164 pages (2003).
L. Robles and M. Ruggero, "Mechanics of the Mammalian Cochlea," Physiological Reviews 81(3):1305-1352 (2001).
J. T. Rubinstein, "How cochlear implants encode speech," Curr Opin Otolaryngol Head Neck Surg 12:444-448 (2004).
R. Saba, "Cochlear implant modeling: Stimulation and power consumption," Ph.D. Thesis, University of Southampton, 224 pages (2012).
J. Sader, "Frequency response of cantilever beams immersed in viscous fluids with applications to the atomic force microscope," Journal of Applied Physics 84(1):64-76 (1998).
A. Sanz-Hervas, et al., "Degradation of the piezoelectric response of sputtere c-axis AlN thin films with traces of non-(0002) x-ray diffraction peaks," Applied Physics Letters 88:161915 (2006).
J. Sarant, "Cochlear Implants in Children: A Review," Chapter 15 "Hearing Loss", book edited by S. Naz, pp. 331-382 (2012); ISBN 978-953-51-0366-0.
S. Shah, et al., "Electrical properties of retinal-electrode interface," J. Neural. Eng. 4:S24-S29 (2007).
S. Shibata, et al., "Transgenic BDNF induces nerve fiber regrowth into the auditory epithelium in deaf cochleae," Experimental Neurology 223(2):464-472 (2010).
H. Shintaku, et al., "Development of a piezoelectric acoustic sensor with frequency selectivity for artificial cochlea," Sensors and Actuators A: Physical 158:183-192 (2010).
V. Thakar, et al., "Acoustically Coupled Thickness-Mode AlN-on-Si Band-Pass Filters—Part II: Simulation and Analysis," IEEE Transactions on Ultrasonics, Ferroelectrics, and Frequency Control 59(10):2270-2277 (2012).
J. Thornton, "The microstructure of sputter-deposited coatings," J. Vac. Sci.Technol. A 4(6):3059-3065 (1986).
E. Tuck, "Calculation of Unsteady Flows Due to Small Motions of Cylinders in a Viscous Fluid,"Journal of Engineering Mathematics 3(1):29-44 (1969).
M. Tykocinski, L. Cohen, and R. Cowan, "Measurement and Analysis of Access Resistance and Polarization Impedance in Cochlear Implant Recipients," Otology & Neurotology 26:948-956 (2005).
C. Vancura, et al., "Analysis of resonating microcantilevers operating in a viscous liquid environment," Sensors and Actuators A 141:43-51 (2008).

(56) References Cited

OTHER PUBLICATIONS

F. G. Zeng, "Cochlear Implants: Why don't more people use them?" Viewpoint: The Hearing Journal, 60(3): 48-49 (2007).
W. Hemmert, et al., "A Life-Sized, Hydrodynamical, Micromechanical Inner Ear," Biophysics of the Cochlea, World Scientific, pp. 409-416 (2003); ISBN: 981-238-304-2.
T. Lechner, "A Hydromechanical Model of the Cochlea with Nonlinear Feedback Using PVF2 Bending Transducers," Hearing Research 66:202-212 (1993).
M. Wittbrodt, et al., "Developing a Physical Model of the Human Cochlea Using Microfabrication Methods," Audiol. Neurotol. 11:104-112 (2006).
M. Bachman, et al., "Micromechanical Resonator Array for an Implantable Bionic Ear," Audiol. Neurotol. 11:95-103 (2006).
F. Chen, et al., "A Hydromechanical Biomimetic Cochlea: Experiments and Models," J. Acoust. Soc. Am, 119(1):394-405 (1996).
D. Haronian and N. MacDonald, "A Microelectromechanics Based Artificial Cochlea," IEEE Transducers '95, 708-711 (1995).
S. Kim, et al., "Mechanical frequency selectivity of an artificial basilar membrane using a beam array with narrow supports," J. Micromech. Microeng. 23:1-13 (2013).
K. Tanaka, et al., "A Novel Mechanical Cochlea "Fishbone" with Dual Sensor/Actuator Characteristics," IEEE/ASME Trans. Mechatronics, 3(2):98-105 (1998).
N. Mukherjee and R. D. Roseman, "Considerations in the Development of a Piezoelectric Transducer Cochlear Implant," Mat. Res. Symp. Proc., vol. 604:79-84 (2000).
T.E. Bell, et al., "A Flexible Micromachined Electrode Array for a Cochlear Prosthesis," Sens. Actuat. A 66:63-69 (1998).
K.D. Wise, et al., "High-Density Cochlear Implants with Position Sensing and Control," Hearing Research, 242:22-30 (2008).
S. Ando, K. Tanaka, and M. Abe, "Fishbone Architecture: An Equivalent Mechanical Model of Cochlea and Its Application to Sensors and Actuators," Transducers '97 Chicago, Solid-State Sensors and Actuators, 1997 International Conference on, vol. 2, pp. 1027-1030 (Jun. 16-19, 1997).
S. M. Antonio, A. D. Meyers, and B. Strasnick. Syndromic sensorineural hearing loss. Online, Apr. 2012.
B. Y. Arcand, et al., "Active positioning device for a perimodiolar cochlear electrode array," Microsystem Technologies, 10:478-483 (2004).
A. Artieda, et al., "Effect of substrate roughness on c-oriented AlN thin films," J. Appl. Phys., 105, 024504 (2009).
A. Artieda, C. Sandu, and P. Muralt, "Highly piezoelectric AlN thin films grown on amorphous, insulating substrates," J. Vac. Sci. Technol. A, 28(3):390-393 (2010).
P. T. Bhatti, et al., "A high density electrode array for a cochlear prosthesis," In the 12th International Conference on Solid State Sensors, Actuators and Microsystems, pp. 1750-1753 (2003).
P. Bhatti and K. Wise, "A 32-Site 4-Channel High-Density Electrode Array for a Cochlear Prosthesis," IEEE Journal of Solid-State Circuits, 41(12):2965-2973 (2006).
R. Bilger, "Psychoacoustic Evaluation of Present Prostheses," Ann Otol Rhinol Laryngol Suppl, (3 Pt 3 Suppl 38):92-104 (1977).
R. Briggs, et al., "Initial Clinical Experience With a Totally Implantable Cochlear Implant Research Device," Otology & Neurotology, 29(2):114-119 (2008).
S. Brummer and M. Turner, "Electrical stimulation of the nervous system: The principle of safe charge injection with noble metal electrodes," Bioelectrochemistry and Bioenergetics, 2(1):13-25 (1975).
M. Bulcke, et al., "Active Electrode Arrays by Chip Embedding in a Flexible Silicone Carrier," Proceedings of the 28th IEEE EMBS Annual International Conference, New York City, USA, Aug. 2006, pp. 2811-2815.
C. Cancelli, S. D'Angelo, M. Masili, and R. Malvano, "Experimental results in a physical model of the cochlea," J. Fluid Mech., 153:361-388 (1985).
F. Chen, et al., "A hydromechanical biomimetic cochlea: Experiments and models," J. Acoust. Soc. Am., 119(1):394-405 (2006).

M. Clement, et al., "Influence of sputtering mechanisms on the preferred orientation of aluminum nitride thin films," Journal of Applied Physics, 94(3):1495-1500 (2003).
S. F. Cogan, "Neural Stimulation and Recording Electrodes," Annu. Rev. Biomed. Eng., 10:275-309 (2008).
S. Crandall, "The Role of Damping in Vibration Theory," J. Sound Vib., 11(1):3-18 (1970).
A. Dancer and R. Franke, "Intracochlear Sound Pressure Measurements in Guinea Pigs," Hearing Research, 2:191-205 (1980).
R. Deng, P. Muralt, and D. Gall, "Biaxial texture development in aluminum nitride layers during off-axis sputter deposition," J. Vac. Sci. Technol. A 30(5)/051501 (2012).
M. Dubios and P. Muralt, "Stress and piezoelectric properties of aluminum nitride thin films deposited onto metal electrodes by pulsed direct current reactive sputtering," J. Appl. Phys. 89(11):6389-6395 (2001).
I. Dufour, et al., "Effect of hydrodynamic force on microcantilever vibrations: Applications to liquid-phase chemical sensing," Sensors and Actuators B: Chemical 192:664-672 (2014).
V. V. Felmetsger, P. N. Laptev, and R. J. Graham, "Deposition of ultrathin AlN films for high frequency electroacoustic devices," J. Vac. Sci. Technol. A 29(2)/021014 (2011).
V. V. Felmetsger, P. Leptev, and S. Tanner, "Innovative technique for tailoring intrinsic stress in reactively sputtered piezoelectric aluminum nitride films," J. Vac. Sci. Technol. A 27(3):417-422 (2009).
C. Fielden, K. Kluk, and C. McKay, "Place specificity of monopolar and tripolar stimuli in cochlear implants: The influence of residual masking," J. Acoust. Soc. Am. 133(6):4109-4123 (2013).
C. C. Finley and M. W. Skinner, "Role of Electrode Placement as Contributor to Variability in Cochlear Implant Outcomes," Otology & Neurotology 29(7):920-928 (2008).
T. Francart and H. McDermott, "Psychophysics, Fitting, and Signal Processing for Combined Hearing Aid and Cochlear Implant Stimulation," Ear and Hearing 34(6):685-700 (2013).
W. Franks, et al., "Impedance Characterization and Modeling of Electrodes for Biomedical Applications," IEEE Transactions on Biomedical Engineering 52(7)1295-1302 (2005).
L. Geddes and R. Roeder, "Criteria for the Selection of Materials for Implanted Electrodes," Annals of Biomedical Engineering 31:879-890 (2003).
D. D. Greenwood, "A cochlear frequency-position function for several species—29 years later," J. Acoust. Soc. Am., 87(6):2592-2605 (1990).
N. Hagood and A. von Flotow, "Damping of Structural Vibrations with Piezoelectric Materials and Passive Electrical Networks," Journal of Sound and Vibration 146(2):243-268 (1991).
M. Harada, et al., "Fish-bone structured acoustic sensor toward silicon cochlear systems," Proc. SPIE Conf. on Micromach. Dev. and Comp. IV, 3514:266-275 (1998).
D. Haronian and N. MacDonald, "A microelectromechancis based artificial cochlea (MEMBAC)," The 8th International Conference on Solid-State Sensors and Actuators, and Eurosensors IX (Transducers '95), pp. 708-711 (1995).
H. Hosaka and K. Itao, "Coupled Vibration of Microcantilever Array Induced by Airflow Force," Transactions of the ASME 124:26-32 (2002).
W. House and J. Urban, "Long Term Results of Electrode Implantation and Electronic Stimulation of the Cochlea in Man," Ann Otol Rhinol Laryngol 82:504-1973 (1973).
G. L. Huffman, et al., "Stress dependence of Reactively Sputtered Aluminum Nitride Thin Films on Sputtering Parameters," J. Vac. Sci. Technol. A 7(3):2252-2255 (1989).
S. Hur, S. Lee, and H. Choi, "Fabrication and characterization of PMN-PT single crystal cantilever array for cochlear-like acoustic sensor," Jour. Mech. Sci. Tech. 24:181-184 (2010).
H. Windischmann, "Intrinsic Stress in Sputter-Deposited Thin Films," Critical Reviews in Solid State and Materials Sciences 17(6):547-596 (1992).
E. Iborra, et al., "Role of Argon Ion Bombardment in Sputtered AlN Films for SAW Devices," 2002 IEEE Ultrasonics Symposium, pp. 411-414 (2002).

(56) References Cited

OTHER PUBLICATIONS

E. Iborra, et al., "Piezoelectric Properties and Residual Stress of Sputtered AlN Thin Films for MEMS Applications," Sensors and Actuators A 115:501-507 (2004).
G. von Bekesy, "Experiments in Hearing," McGraw-Hill, 3 pages (1960).
G. von Bekesy, "Concerning the pleasures of observing, and the mechanics of the inner ear," In Nobel Lecture, 25 pages (1961).
L. Waaijer, et al, "The Peripheral Processes of Spiral Ganglion Cells After Intracochlear Application of Brain-Derived Neurotrophic Factor in Deafened Guinea Pigs," Otology & Neurotology 34:570-578 (2013).
J. Wang, M. Gulari, and K. Wise, "A Parylene-Silicon Cochlear Electrode Array with Integrated Position Sensors," Proceedings of the 28th IEEE EMBS Annual International Conference, New York City, USA, pp. 3170-3173 (Aug. 30-Sep. 3, 2006).
J. Weiland and D. Anderson, "Chronic Neural Stimulation with Thin-Film, Iridium Oxide Electrodes," IEEE Transactions on Biomedical Engineering 47(7)911-918 (2000).
M. Wittbrodt, C. Steele, and S. Puria, "Developing a Physical Model of the Human Cochlea using Microfabrication Methods," Audiology & Neurotology 11:104-112 (2006).
F. Wu, et al., "A multi-shank silk-backed parylene neural probe for reliable chronic recording," In 2013 Transducers Eurosensors XXVII: The 17th International Conference on Solid-State Sensors, Actuators and Microsystems (Transducers Eurosensors XXVII), pp. 881-891 (2013).
T. Xu, et al., "Polymeric micro-cantilever array for auditory front-end processing," Sensors and Actuators A 114:176-182 (2004).
M. Yip, et al., "A Fully-Implantable Cochlear Implant SoC with Piezoelectric Middle-Ear Sensor and Energy-Efficient Stimulation in 0.18µm HVMOS," 2014 IEEE International Solid-State Circuits Conference, pp. 312-314 (2014).
D. Young, et al., "MEMS Capacitive Accelerometer-Based Middle Ear Microphone," IEEE Transactions on Biomedical Engineering 59(12):3283-3292 (2012).
F. Zeng, et al., "Cochlear Implants: System Design, Integration, and Evaluation," IEEE Reviews in Biomedical Engineering 1:115-142 (2008).
G. Zhou, et al. "A life-sized physical model of the human cochlea with optical holographic readout," J. Acoust. Soc. Am. 93(3):1516-1523 (1993).

D. Zhuang and J. H. Edgar, "Wet etching of GaN, AlN, and SiC: a review," Materials Science and Engineering R 48:1-46 (2005).
G. Loeb, "The Functional Replacement of the Ear," Scientific American, Inc. © 1985, 8 pages.
Illustration from Kids Health: Cochlear Implants by Nemours Foundation, ©1995-2013, 7 pages.
K. Tsubouchi, et al., "AlN Material Constants Evaluation and SAW Properties on AlN/Al2O3 and AlN/Si," Proceedings of the IEEE Ultrasonic Symposium, pp. 375-389 (1981).
R. White, "Biomimetic Trapped Fluid Microsystems for Acoustic Sensing," Ph.D. Dissertation, University of Michigan, 256 pages (2005).
B. Blausen, Anatomy of the Ear Illustration, Online (2013), https://en.wikiversity.org/wiki/File:Blausen_0328_EarAnatomy.png.
B. Blausen, Cochlear Implant Illustration, Online (2013), https://en.wikiversity.org/wiki/File:Blausen_0244_CochlearImplant_01.png.
B. Blausen, Internal Ear Anatomy Illustration, Online (2013), https://en.wikiversity.org/wiki/File:Blausen_0329_EarAnatomy_InternalEar.png.
R. Chaikof, M. Chaikof, and E. Rosenzweig—Brand Comparison Chart—Choosing a Cochlear Implant Brand; Cochlear Implant Online ©2013; http://cochlearimplantonline.com/site/cochlear-implant/brand-names/brand-comparison-chart/.
The Cochlea, Springer Handbook of Auditory Research, Table of Contents, Editors: P. Dallos, A. Popper, R. Fay, Springer-Verlag, New York, Inc. ©1996.
C. D. Geisler, From Sound to Synapse—Physiology of the Mammalian Ear, Table of Contents, Oxford University Press, ©1998.
J. Holt, S. Hotto, and K. Cole, "Demographic aspects of hearing impairment: Questions and answers," Third edition, (1994); https://research.gallaudet.edu/Demographics/factsheet.php.
S. Koshigoe and A. Tubis, "A Non-Linear Feedback Model for Outer-Hair-Cell Stereocilia and Its Implications for the Response of the Auditory Periphery," Mechanics of Hearing, E. de Boer et al. (eds.) © Delft Univ. Press, The Netherlands (1983).
Semiconductor Materials and Process Technology Handbook for Very Large Scale Integration (VLSI) and Ultra Large Scale Integration (ULSI), G. McGuire, editor, ©1988 William Andrew Publishing/Noyes.
NICD Fact Sheet—Cochlear Implants, National Institute on Deafness and Other Communication Disorders (2011); http://www.nicd.nih.gov.
Z. Deretsky, National Science Foundation School Textbooks Online, Class 11: Biology, Ch. 21, Available at: http://textbook.s-anand.net/ncert/class-11/biology/21-neural-control-and-coordination.

Electrode Bundle

COCHLEAR IMPLANT

CROSS REFERENCE TO RELATED APPLICATIONS

This application claims priority to and all the benefits of U.S. Provisional Patent Application Ser. No. 61/940,709 filed on Feb. 17, 2014, the contents of which are expressly incorporated herein by reference in their entirety.

FIELD OF THE DISCLOSURE

The present disclosure relates generally to cochlear implants and, more particularly, to a device to be implanted into a scalia tympani of a cochlea.

BACKGROUND

The cochlea is an organ in the inner ear that converts sound vibrations into electrical signals, and the electrical signals are transmitted to the brain by the auditory nerve. The cochlea has a scala tympani, scala media, and a scala vestibule, which are fluid-filled ducts separated by a tapered membrane called the basilar membrane. As shown in FIG. 1, mechanical impedance changes along the basilar membrane typically causes tonotopic filtering along the length of the basilar membrane allowing high frequency sounds to resonate near the base of the cochlea and lower frequency sounds to travel through the cochlea and resonate near the apex of the cochlea.

The organ of Corti is supported by the basilar membrane and houses sensory cells of the cochlea. Typically, a patient with sensorineural hearing loss has malfunctioning or nonexistent sensory cells housed by the organ of Corti, but has a functioning auditory nerve. Cochlear implants are often used to replace these malfunctioning or nonexistent sensory cells.

Cochlear implants typically have the ability to restore 80 to 90% of word recognition hearing in a patent having sensorineural hearing loss. An example of a traditional cochlear implant is shown in FIGS. 2A, 2B, and 2C. This traditional cochlear implant is powered by a battery and includes an external microphone and an external sound processing unit positioned behind the ear (FIG. 2A). The traditional cochlear implant further includes an inductive link that transmits power and information from an external unit to a receiving unit disposed in subcutaneous tissue of the ear (FIG. 2B). Further, a probe with a flexible silicone shank having an array of platinum or platinum-iridium electrodes and two ground electrodes is inserted into the cochlea (FIG. 2C). The probe is typically surgically implanted into the scala tympani of the cochlea, and is wound through the cochlea.

Traditional cochlear implants, such as the cochlear implant described above with reference to FIGS. 2A, 2B, and 2C, typically have an undesirably large power consumption (e.g. the battery may last up to only about 5 days), has high latency, is relatively expensive, and the probe is difficult to insert into the cochlea. Additionally, due to the inflexibility of the probe, the basilar membrane may get punctured during implantation of the probe into the cochlea which can further damage hearing loss. The cochlear implants that are currently available are also often difficult for use in sporting activities and under water (such as in a shower).

Fully implantable cochlear implants have been studied. However, none of these fully implantable cochlear implants achieve a desired sensitivity and none are easy to implant into the curved cochlea.

Accordingly, there remains an opportunity to develop an implantable cochlear implant that is flexible in the plane of curvature of the cochlea and is implantable without damaging the basilar membrane.

SUMMARY OF THE DISCLOSURE

In one embodiment, the present disclosure describes a device for implantation into a scalia tympani of a cochlea that is connected to an auditory nerve with the cochlea having a plane of curvature and including a cochlear fluid. The device comprises a plurality of blocks. The device further comprises a plurality of compliant elements interconnecting the plurality of blocks for imparting flexibility to the device in the plane of curvature of the cochlea and for imparting stiffness to the device out of the plane of curvature of the cochlea. The device further comprises a plurality of piezoelectric elements with at least one of the plurality of piezoelectric elements disposed on at least one of the blocks with each of said plurality of piezoelectric elements comprising at least one piezoelectric sensing unit for sensing vibration of the cochlear fluid inside the cochlea and for converting the vibration into an electrical signal and at least one electrode for transmitting the electrical signal to the auditory nerve. The device further comprises a plurality of communication lines for transmitting the electrical signal through the device with one of the plurality of communication lines disposed between each of the pair of adjacent blocks and adjacent the compliant element.

In another embodiment, the present disclosure describes a device for partial implantation into a scalia tympani of a cochlea that is connected to an auditory nerve with the cochlea having a plane of curvature and including cochlear fluid. The device comprises a plurality of blocks. The device further comprises a plurality of compliant elements interconnecting the plurality of blocks for imparting flexibility to the device in the plane of curvature of the cochlea and for imparting stiffness to the device out of the plane of curvature of the cochlea. The device further comprises a processing unit external to the cochlea for processing sound into an electrical signal. The device further comprises a plurality of electrodes with at least one of the electrodes disposed on each of said blocks, the plurality of electrodes for transmitting the electrical signal to the auditory nerve. The device further comprises a plurality of communication lines for transmitting the electrical signal through said device with one of the plurality of communication lines disposed between each of the pair of adjacent blocks and adjacent the compliant element.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1:
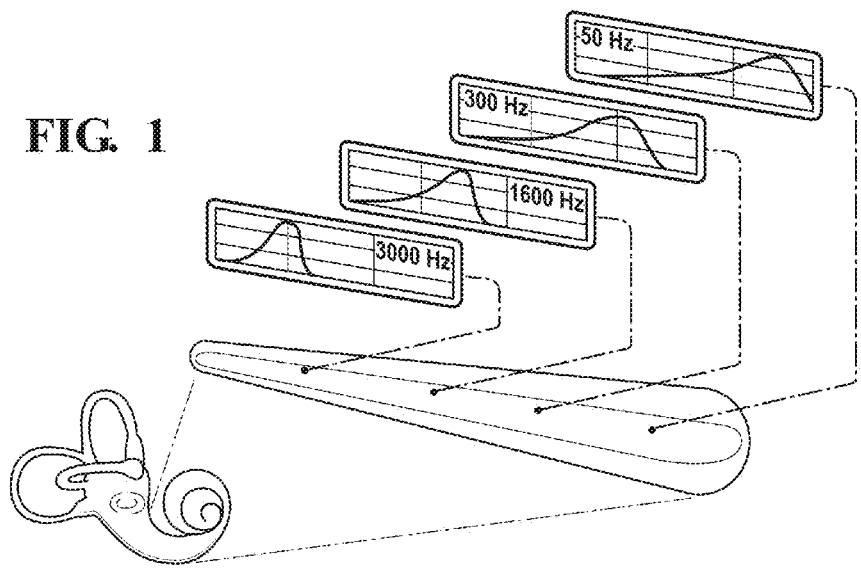
FIG. 1 is a diagram illustrating the tonotopic frequency filtering of the cochlea.
Figure 2A:
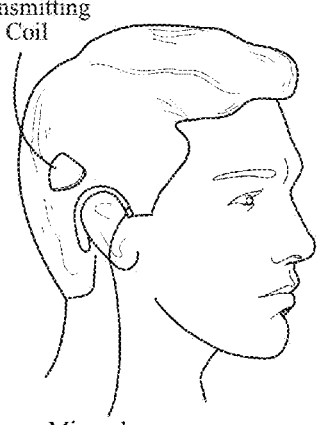
FIGS. 2A, 2B, and 2C together illustrate an example of a traditional cochlear implant system.
Figure 2B:
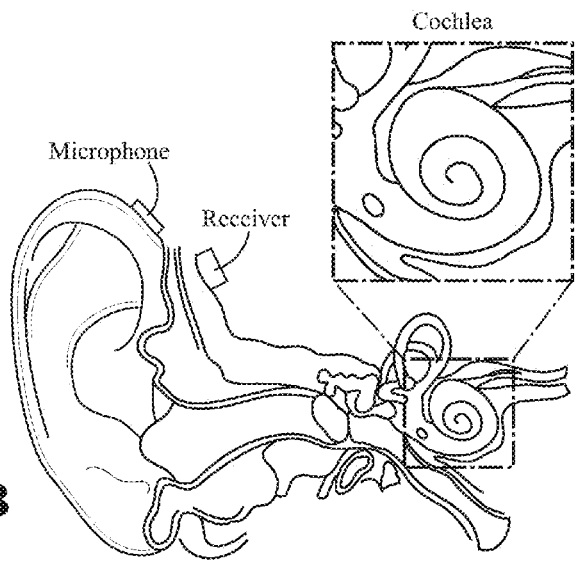
Figure 2C:
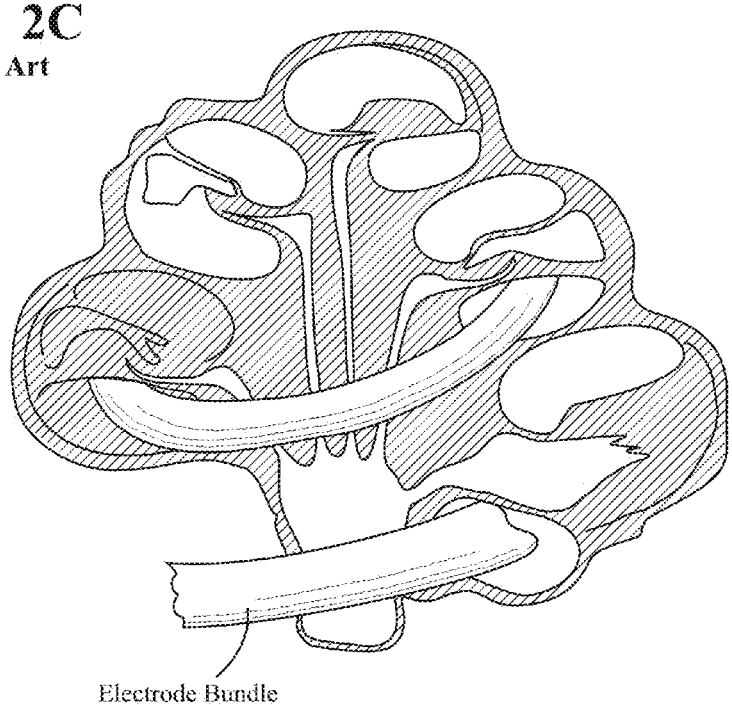

Referring now to the Figures, where like numerals indicate like or corresponding parts throughout the several views, various embodiments of a device to be implanted into the scala tympani of the cochlea is shown and described herein. In an embodiment, the device 100 is implantable into the scala tympani of the cochlea. Further, in this embodiment, the device 100 is fully implantable in the cochlea; i.e., the entire device 100 can be implanted into the cochlea. In an embodiment, the device 100 is configured to transduce mechanical vibrations of the cochlear fluid into electrical signals that stimulate the auditory nerves without utilizing an external sound processing unit (i.e., a sound processing unit which is external to the cochlea). In another embodiment, the device 100 comprises piezoelectric elements 106, such as piezoelectric cantilevers. Vibrations in the cochlear fluid deflect the piezoelectric cantilevers 106 resulting in a potential forming on outer or top electrodes of the cantilever 106. The top electrodes 116 may, for instance, be in contact with the ionic fluid of the cochlea and produce a current in the cochlear fluid that is passed to and stimulates the auditory nerves. This embodiment describes a passive case. Top and bottom electrodes 116, 108 of the piezoelectric cantilevers 106 may be grounded, and a middle electrode 112 of the piezoelectric cantilevers 106 may have an amplified voltage that is sent to a separate stimulating electrode positioned next to the cantilever 106. The stimulating electrode 124 may then be in contact with the ionic fluid of the cochlea and produces a current in the cochlear fluid that is passed to and stimulates the auditory nerves. This embodiment describes an active case.

An embodiment of the device 100 is described below at least with reference to FIGS. 3-7. This device 100 is implantable into the cochlea. The device 100 comprises an implantable flexible probe 102 having a plurality of sequentially arranged blocks 104 and a plurality of piezoelectric elements 106, such as piezoelectric cantilevers. Each cantilever 106 comprises at least one piezoelectric sensing unit 110, 114. The probe 102 functions as an artificial cochlea, and may be used as a long term implant.

Each block 104 consists of or comprises an insulating material, semi-conducting material, a conducting material, and/or combinations thereof. In an embodiment, each block 104 consists of or comprises silicon. In another embodiment, the blocks 104 consist of or comprise a material selected from silicon, silicon oxides, silicones, polyimides, and/or combinations thereof. The length and/or width of each block 104 may, for example, be from 100 μm to 1 mm. The length and/or width of each block 104 may, in another example, be from 200 to 500 μm. In an embodiment, each block 104 may have substantially the same length. In another embodiment, one or more of the blocks 104 may have a length that is different from one or more other blocks 104. Said differently, the lengths of the blocks 104 may be varied. Additionally, the thickness of each block 104 may, for example, be from 10 to 650 μm. The thickness of each block 104 may, in another example, be from 200 to 500 μm. The ranges for the length, width, and/or thickness are for a device 100 to be implanted into a guinea pig. Accordingly, the length, width, and/or thickness of the block 104 may be as large as 1.5 mm if the device 100 is implanted into a human. Additionally, the shapes of the blocks 104 may vary. In one example, the blocks 104 may have a triangular shape in the direction in the plane of the cochlea. In another example, the blocks 104 may face parallel to the plane of the cochlea and have a rectangular shape with rounded edges. It is to be understood that all values and ranges of values therebetween are contemplated in non-liming embodiments.

Figure 4A:
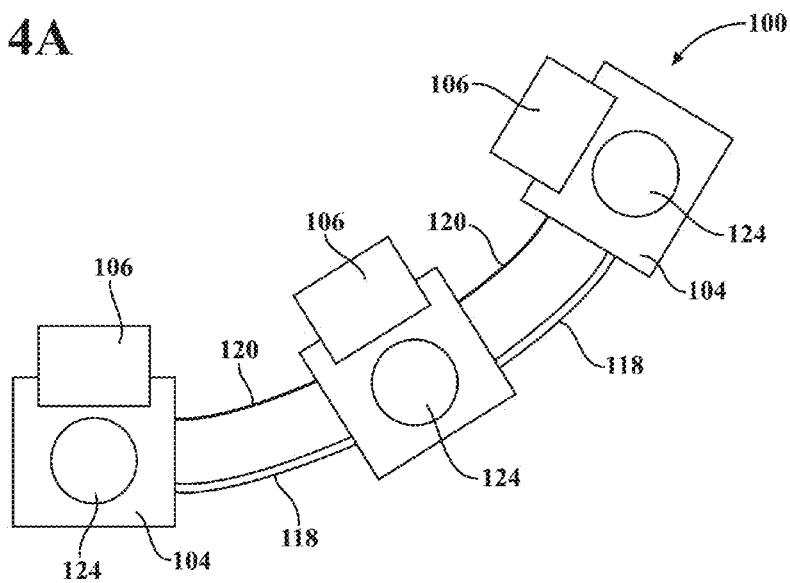
FIG. 4A schematically illustrates a plan view of the device shown in FIG. 3.

As shown in FIG. 4A, the probe 102 further comprises a plurality of compliant elements 118 interconnecting the plurality of blocks 104. The combination of the blocks 104 and the compliant elements 118 typically form a backbone of the probe 102. In an embodiment, the probe 102 may have a length of from 2.5 mm to 3 cm. For use in humans, and in another embodiment, the probe 102 may have a length of from 1 cm to 2 cm. For use in a guinea pig, in still another embodiment, the probe 102 may have a length of from 2.5 mm to 1.5 cm. Further, the probe 102 may have, for example, from 3 to 10 blocks 104. The probe 102 may have, in another example, from 5 to 7 blocks 104. The probe 102 may have any number of blocks 104 so long as the probe 102 can sufficiently be implanted into the cochlea.

The compliant element 118 is typically disposed between adjacent blocks 104. In another embodiment, the compliant element 118 may be embedded at either end in the blocks 104 (such as by etching trenches in the blocks 104 and incorporating the compliant element 118 into the trenches). The compliant element 118 imparts at least some flexibility to the probe 102 in the plane of curvature of the cochlea. In this way, the probe 102 can be curved and/or bent in the plane of curvature of the cochlea. For instance, the probe 102 can be curved and/or bent to conform to the helical or spiral shape of the cochlea when the device 100 is implanted into the cochlea 10. Due, at least in part, to this flexibility, the device 100 can be fully implanted into the scala tympani of the cochlea without damaging elements of the ear such as the basilar membrane. Additionally, once implanted, the ability of the device 100 to conform to the shape and/or the curve of the cochlea enables the device 100 to reside closer to the auditory nerves. This allows for a better spectral resolution and auditory nerve response. Also by being closer to the nerves, there is less current spreading, lower power consumption, and a greater frequency resolution.

Additionally, the compliant element 118 tends to impart at least some stiffness to the probe 102 out of the plane of curvature of the cochlea. Stiffness out of the plane of curvature and elastic compression in the plane of curvature of the cochlea enable pre-surgical compression of the device 100 into a straight configuration for easily implantation of the device 100 into the cochlea. Stiffness out of the plane of curvature and elastic compression in the plane of curvature of the cochlea also typically enable recoiling of the device 100 (i.e., its uncompressed shape) during implantation to conform to the curved shape of the cochlea.

In an embodiment, the compliant element 118 is a meander spring or a combination of a meander spring and a flexible polymer. Typically, meander springs are flexible U-shaped or V-shaped metal springs, and the geometry of the meander spring may be adjustable for a desired stiffness of the probe 102 in the plane of curvature of the cochlea. In an example, changes to the height of the meander spring may also be used to control the stiffness out of the plane of curvature of the cochlea. The meander springs may consist of or comprise material selected from Au, Pt, Si, Ir, Ni, Cr, Ti, and/or combinations thereof. The meander springs may also or otherwise consist or comprise other metals and/or semiconductive materials. Flexible polymers that may be used in combination with the meander spring include, but are not limited to, silicones, parylenes (such as Parylene C), polyimides, SU-8 (which is an epoxy-based negative photoresist), polymethylmethacrylates, polydimethylsiloxanes, and/or combinations thereof.

Typically, the probe 102 comprises meander springs as the compliant element 118 disposed between each pair of adjacent blocks 104. In some instances, the probe 102 comprises meander springs and flexible polymers (i.e., a combination of meander spring(s) and flexible polymer(s)) between each pair of adjacent blocks 104. For example, and as described in further detail below, the probe 102 comprises meander springs each surrounded or encapsulated with a flexible polymer(s). In an example, the probe 102 comprises a meander spring with a flexible polymer surrounding the meander spring. In yet other instances, one or more of the compliant elements 118 in the probe 102 may be a meander spring while the remaining compliant elements 118 in the probe 102 may be a combination of a meander spring and a polymeric material.

In an embodiment, the meander springs are metallurgically coupled to the blocks 104. For instance, the ends of the compliant element 118 may be metallurgically bonded to adjacent blocks 104 with a suitable metal, such as a sticky metal selected from Cr and/or Ti. For meander springs each in combination with a flexible polymer(s), the flexible polymer(s) may be chemically coupled to the blocks 104. Typically, the flexible material chemically bonds to the blocks 104 on its own. Some materials (such as Parylene C), however, may chemically bond to the blocks 104 with the assistance of an adhesion promoter.

The geometry of the compliant element 118 is not particularly limiting and may be selected based on the curvature of the cochlea in a prescribed location in the cochlea. Furthermore, the length of the compliant element 118 may be selected based on a desired spacing between the blocks 104 to achieve a desired probe compliance.

In an embodiment, the compliant element 118 is a combination of a meander spring and a flexible polymer, where the meander spring is embedded in the flexible polymer. For instance, the meander spring (which may be built up by electroplating or trench refill) may be surrounded with the flexible polymer (which may be injection molded or photopatterned on the built up meander springs).

As previously described, the device 100 comprises a plurality of piezoelectric cantilevers 106. In an embodiment, the piezoelectric cantilevers 106 with at least one of the piezoelectric cantilevers 106 disposed on the blocks 104. In an example, a piezoelectric cantilever 106 may be disposed on each of the blocks 104. In another example, one or more of the blocks 104 may be bare, where such blocks 104 do not have a piezoelectric element 106 disposed on the blocks 104. The piezoelectric cantilevers 106 may, for example, have a rectangular shape. However, the piezoelectric cantilevers 106 may have any desirable shape such as a rectangular shape, a trapezoidal shape, etc., and is therefore not limited in shape. Additionally, and in an embodiment, at least one piezoelectric cantilever 106 may be coupled to or disposed on a block 104. For instance, a single piezoelectric cantilever 106 may be coupled to or disposed on a block 104. In another instance, two or more piezoelectric cantilevers 106 may be coupled to or disposed on a block 102. In these instances, the piezoelectric cantilevers 106 may be stacked or may be positioned adjacent to one another on a single block 104. Further, the piezoelectric cantilevers 106 individually have a length, and the length of a first one of the piezoelectric cantilevers 106 may be different from the length of a second one of the piezoelectric cantilevers 106. In this way, the varying lengths of the piezoelectric cantilevers 106 form cantilevers 106 with a xzlophone arrangement.

Figure 4B:
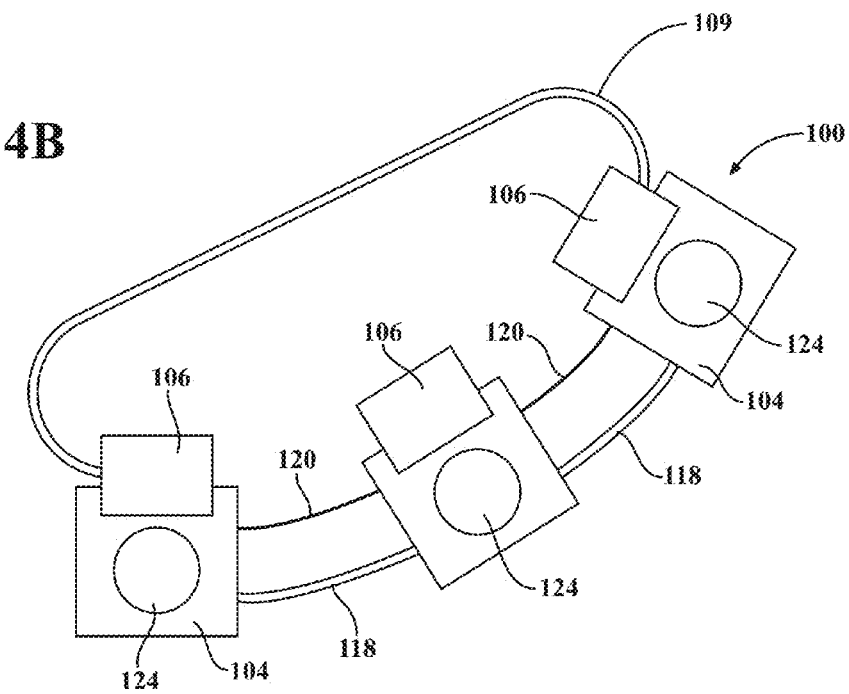
FIG. 4B schematically illustrates a plan view of another embodiment of the device.
Figure 5:
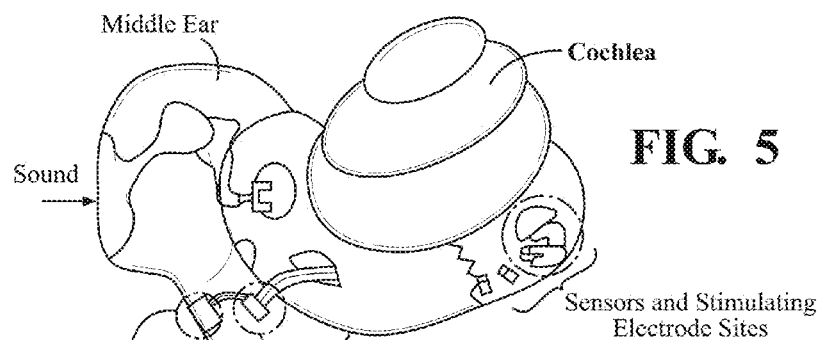
FIG. 5 illustrates the cochlea and the middle ear with the device implanted into the scala tympani of the cochlea.

In an example, and as shown in FIG. 4A, the cantilevers 106 have a fixed-free configuration, where the cantilevers 106 are fixed at the base of the probe 102 and are free on the other end of the probe 102. In another example, and as shown in FIG. 4B, the cantilevers 106 have a fixed-fixed configuration, where the cantilevers 106 are encased by a polymer such as silicon or by some other enclosure 109. Alternatively, the enclosure 109 may encase a single cantilever 106, two cantilevers 106, or more cantilevers 106.

In an embodiment, each piezoelectric cantilever 106 comprises at least one piezoelectric sensing unit 110, 114. In another embodiment, each cantilever 106 comprises two piezoelectric sensing units 110, 114. Each piezoelectric sensing unit 110, 114 may have a width of, for example, from 300 to 500 µm. Each piezoelectric sensing unit 110, 114 may, in another example, have a width of from 380 to 420 µm. Further, the length of the piezoelectric sensing units 110, 114 typically span from 200 to 300 µm. Typically, the width of the piezoelectric sensing unit 110, 114 is constant while the lengths of the piezoelectric sensing unit 110, 114 change across the length of the probe 102. Alternatively, the length of the piezoelectric sensing units 110, 114 may be the same across the length of the probe 102. The width of the piezoelectric sensing unit 110, 114 may otherwise be different across the length of the probe 102. It is to be understood that all values and ranges of values therebetween are contemplated in non-liming embodiments.

Further, each piezoelectric sensing unit 110, 114 may have a thickness of, for example, from 0.3 to 10 µm. The thickness of the piezoelectric sensing units 110, 114 depends, at least in part, on the material of the piezoelectric sensing units 110, 114. For AlN (aluminum nitride) piezoelectric sensing units 110, 114, each AlN piezoelectric sensing unit 110, 114 may have a thickness of from 1.5 to 2.5 µm. In another embodiment, each AlN piezoelectric sensing unit 110, 114 may have a thickness of from 1 to 2 µm.

Thinner piezoelectric sensing units 110, 114 may be used to reduce the effects of electronic noise, such may be due to losses in the material.

Non-limiting examples of materials for the piezoelectric sensing units 110, 114 include lead zirconate titanate (PZT), lead magnesium niobate-lead titanate (PMN-PT), poly L lactic acid (PLLA), aluminum nitride (AlN), ZnO, polyvinylidene fluoride (PVDF), lithium niobate (LiNbO$_3$), aluminum scandium nitride (AlScN), and/or combinations thereof. In one specific embodiment, the piezoelectric sensing units 110, 114 consist of or comprise AlN (aluminum nitride). It is to be understood that all values and ranges of values therebetween are contemplated in non-liming embodiments.

Figure 3:
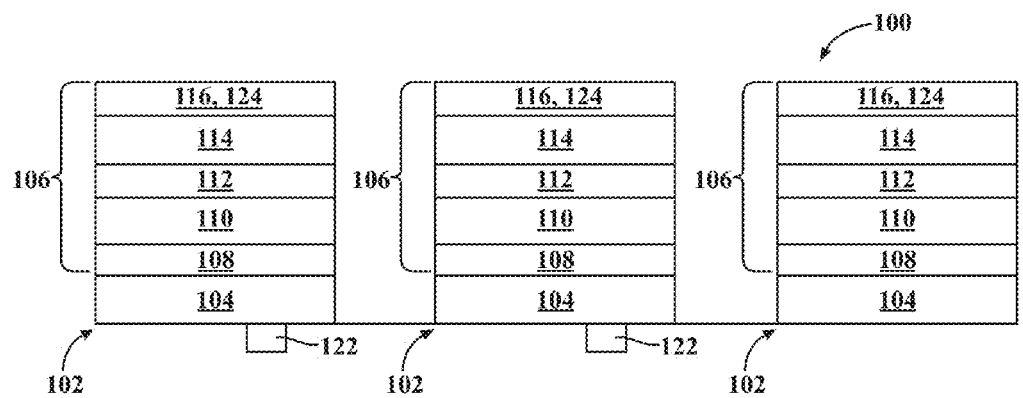
FIG. 3 schematically illustrates a side view of an embodiment of a device to be implanted into a scala tympani of the cochlea.

In one embodiment, each piezoelectric cantilever 106 has an electrode-piezoelectric sensing unit-electrode-piezoelectric sensing unit-electrode configuration. This configuration describes a biomorph configuration, which in this embodiment, has two piezoelectric sensing units 110, 114 surrounded by three electrodes 108, 112, 116. This is shown in FIG. 3. For instance, and as shown, the cantilever 106 comprises a bottom electrode 108 with the first piezoelectric sensing unit 110 disposed on the bottom electrode 108, a middle electrode 112 is disposed on the first piezoelectric sensing unit 110, the second piezoelectric sensing unit 114 is disposed on the middle electrode 112, and a top electrode 116 disposed on the second piezoelectric sensing unit 114. A plurality of cantilevers 106 are disposed (e.g. mounted) on respective blocks 104 to form the probe 102.

As described above, the cantilevers 106 have bottom 108, middle 112, and top 116 electrodes. All of these electrodes 108, 112, 116 comprise a metal. Non-limiting examples of the metal for the electrodes 108, 112, 116 include Pt, Ti, Cr, Au, Ir, IrO, PtIr alloys, and/or combinations thereof. Additionally, the electrodes 108, 112, 116 may have a thickness of, for example, from 20 to 80 nm. In another embodiment, the electrodes 108, 112, 116 may have a thickness of from 40 to 60 nm. It is to be understood that all values and ranges of values therebetween are contemplated in non-liming embodiments.

In an embodiment, the device 100 further comprises a stimulating electrode 124. In the passive case, the stimulating electrode 124 is the top electrode 116 of the piezoelectric cantilever 106. In the active case, the stimulating electrode 124 is another electrode coupled to each block 104 but is separate from the piezoelectric cantilever 106. In an embodiment, the stimulating electrode 124 may have a thickness of from 3 to 10 μm. It is to be understood that all values and ranges of values therebetween are contemplated in non-liming embodiments.

Each piezoelectric cantilever 106 may, for example, be tailored to a specific frequency that matches a tonotopic organization of the cochlea. In use, vibrations of the basilar membrane and its surrounding fluid vibrate the piezoelectric cantilevers 106 to produce a sinusoidal voltage response, which has a relatively narrow bandwidth. This voltage response may be transmitted into the cochlear fluid utilizing the top electrode 116 as the stimulating electrode 124. This scenario describes the passive case. Alternatively, the voltage response may be transmitted to one or more amplifiers 122, to a stimulating electrode 124, and into the cochlear fluid. This scenario describes an amplified or active case. In another embodiment, the amplified response may be fed back into the piezoelectric cantilever 106 in a feedback loop, which mimics the function of the amplifier 124. In this embodiment, a stimulating electrode 124 is not used. The voltage response or the amplified voltage response which is transmitted to the cochlear fluid produces a current in the cochlea fluid which stimulates the auditory nerve.

Furthermore, the length of each of the piezoelectric cantilevers 106 is typically selected based on a resonant frequency of the cochlear fluid. In an embodiment, a selected length of each of the piezoelectric cantilevers 106 may be from 80 to 120 μm based on a resonant frequency of 20 to 40 kHz in the cochlear fluid. It is to be understood that all values and ranges of values therebetween are contemplated in non-liming embodiments.

In another example, each piezoelectric cantilever 106 is not tied to the tonotopic organization or location of the cochlea.

In an embodiment, the resonant frequency of the piezoelectric cantilever 106 immersed in a viscous fluid may be modeled utilizing Euler-Bernoulli equation with a modified β, which is a coefficient that determines resonant frequency. β utilizes all of the geometric information of the cantilever 106, as well as the mass of the cantilever 106. The resonant frequency of the piezoelectric cantilever 106 (β) is also modeled as a function of varied lengths and widths for a prescribed thickness of the piezoelectric sensing units 110, 114. The modified Euler-Bernoulli equation is set forth below as Equation (1):

$$\frac{d^4 W(x/\varpi)}{dx^4} - \beta^4(x/\varpi) = F_{mech}(x/\varpi)\frac{L^4}{YI} \qquad \text{(Eqn. 1)}$$

where x is the location along the cantilever 106 measured in meters, W is the deflection which is the vertical height displacement from x measured in meters, L is the length of the piezoelectric cantilever 106 measured in meters, $F_{mech}$ is any force along the length of the cantilever 106 measured in Newtons, Ω is the frequency in Hz, Y is Young's Modulus measured in Pascals, and I is the moment of inertia for the cantilever 104 measured in Kg*m$^2$.

In Equation 1, β (which is a unitless number) has been modified to include a viscous fluid damping term (($\pi \rho b^2$)/(4Q)) and a structural damping term ($c_{sd}$ which is a constant), as shown in Equation (2) below:

$$\beta^4 = \frac{\rho A_0 \varpi^2 L^4}{YI}\left(1 + \frac{\pi \rho b^2}{4\mu}\Gamma(\varpi) - \frac{jc_{sd}}{\rho A_0 \varpi}\right) \qquad \text{(Eqn. 2)}$$

In Equation 2, the hydrodynamic function Γ(Ω) is a dimensionless term that corrects the hydrodynamic forcing term based on the cross-sectional area of the piezoelectric sensing unit 108. For instance, Γ(Ω) is a term that is used to convert standard hydrodynamic loading for a circular cantilever into a force suitable for a cantilever having a rectangular cross-section. The hydrodynamic function Γ(Ω) may be determined using the calculation set forth in J. E. Sader "Frequency Response of Cantilever Beams Immersed in Viscous Fluids with Applications to the Atomic Force Microscope," J. Appl. Phys., 84:64-76, 1998, the relevant contents of which are incorporated herein by reference in their entirety. Further, in Equation 2, ρ is the fluid density measured in Kg/m$^3$, μ is the mass per unit length measured in Kg/m, L is the length of the piezoelectric cantilever 106 measured in meters, Ω is the frequency in Hz, Y is the Young's Modulus, I is the moment of inertia for the cantilever 106, and b is the width of the piezoelectric cantilever 106 measured in meters.

The device 100 further comprises a communication line 120 (such as a wire, a series of wires, or a cable) which may be disposed between adjacent blocks 104 and positioned parallel to the compliant element 118. The communication line 120 comprises a flexible polymer that is metallized to provide electrical connectivity between adjacent piezoelectric cantilevers 106. In an embodiment, the flexible polymer for the communication line 120 may be selected from any of the flexible polymers identified above for the compliant element 118. Further, metallization of the flexible polymer may be accomplished by incorporating a metal into the flexible polymer. Non-limiting examples of metals that may be incorporated into the communication line include Au, Pt, Cr, Ti, Ni, Cu, Mo, Ir, and/or combinations thereof.

Figure 6:
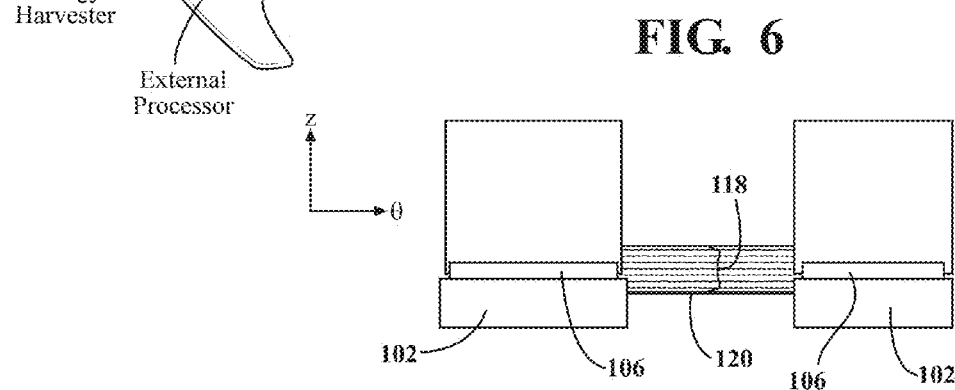
FIG. 6 is a side view of an enlarged portion of the device shown in FIG. 3.
Figure 7:
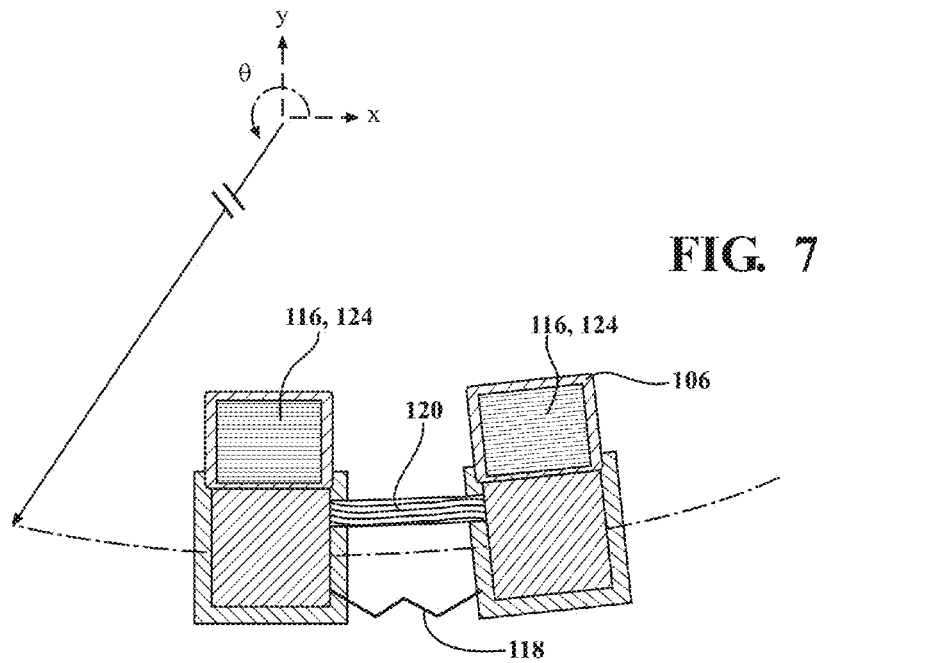
FIG. 7 is a plan view of an enlarged portion of the device shown in FIG. 3.

As previously described, the communication line 120 provides electrical connectivity between the piezoelectric cantilevers 106. The communication line 120 also provides stiffness to the compliant element 118 that is out of the plane of curvature of the cochlea. In an embodiment, and as shown in FIGS. 6 and 7, stiffness that is out of the plane of curvature of the cochlea may be controlled by controlling the height (in the z-axis) of the compliant element 118. Additionally, the communication line 120 contributes to stiffness about the z-axis based, at least in part, on the width of the communication line 120. In an embodiment, the width of the communication line 120 may be from 2 µm to 1 mm. In another embodiment, the width of the communication line 120 may be from 50 to 250 µm. Typically, the communication line 120 varies in width across the length of the probe 102, where the communication line 120 may be wider at the base of the probe 102 and narrower at the tip of the probe 102.

In an embodiment, the probe 102 further comprises a block 104 at an end of the probe 102 which serves as an anchor point for the probe 102. This block 104 also provides a space for attachment of the communication line 120. Further, the device 100 may be powered through the communication line 120 that connects to a transceiver unit (not shown) that is supplied with external power (such as a battery) or connects to an energy harvester. This is shown, for example, in FIG. 5.

In an embodiment, one or more amplifier(s) 122 may be coupled to the one or more of the blocks 104 of the probe 102, and communication with the amplifier(s) 122 is accomplished using the communication line 120. Alternatively, the amplifier 122 may be housed in an amplifier block (not shown) coupled to the probe 102 by a cable. In this case, signals from a transducer are communicated from the piezoelectric cantilevers 106 to the amplifier 122, and the amplified signals are sent back to the piezoelectric cantilevers 106 in a feedback loop. This mimics the efferent function of the cochlea. Alternatively, the amplified signals are sent to a separate set of stimulating electrodes 116, 124.

Figure 11:
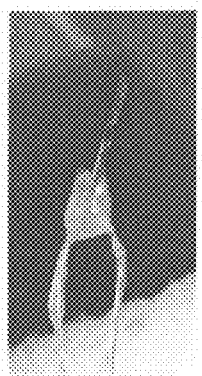
FIG. 11 is a photograph of a prototype of the device which is implantable in the cochlea.
Figure 12:
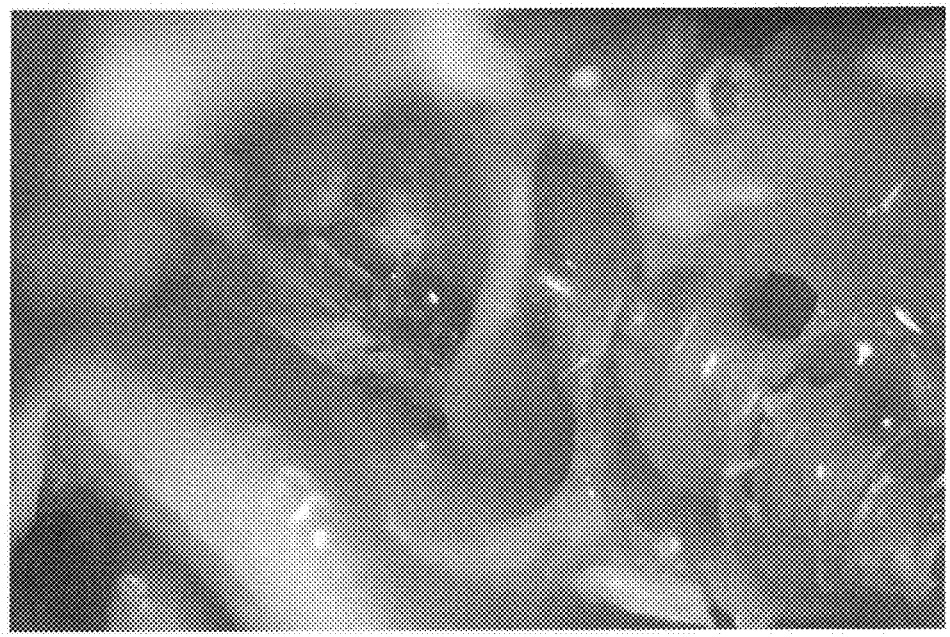
FIG. 12 is a photograph of the prototype of the cochlear implant of FIG. 11 implanted into the cochlea of a guinea pig.

A prototype of a fully implantable cochlear implant (i.e., the device 100) was fabricated and implanted into a guinea pig for one week. A photograph of the prototype of the implant probe of the fully implantable cochlear implant is shown in FIG. 11. A photograph of the prototype implant probe during implantation into the cochlea of the guinea pig is shown in FIG. 12.

The device 100 may be fabricated utilizing a microelectromechanical systems (MEMS) batch processing method. The method involves forming the piezoelectric cantilevers 106, disposing one of the piezoelectric cantilevers 106 on a respective one of the plurality of blocks 104, disposing a compliant element 118 between each pair of adjacent blocks 104 for interconnecting the blocks 104, and disposing a communication line 120 between each pair of blocks 104 adjacent to the compliant element 118.

Figure 9A:
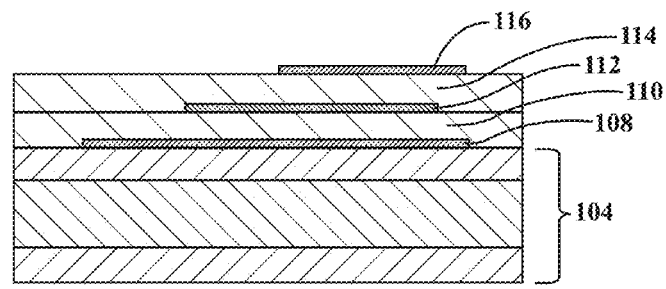
FIGS. 9A-9D schematically illustrate steps in a fabrication process of a device to be implanted into the cochlea.

An example of the steps of forming the piezoelectric cantilevers 106 and disposing the piezoelectric cantilevers 106 on the blocks 104 is described below with reference to FIGS. 9A-9D. As shown in FIG. 9A, the method includes providing the block 104, such as a 4 inch thick, double sided polished p-type silicon wafer. In an example, the silicon wafer is coated with a thin layer (e.g., about 1 µm thick) of a thermal oxide, which serves as an electrical insulation layer. In an example, one or both of the thermal oxide layers may be etched to reduce the thickness of the layer(s), such as to about 1 µm.

The method further includes forming the bottom electrode 108 on the block 104 by deposition and patterning using, for example, a photolithography process with a metal. For example, a Ti/Pt layer is sputter deposited and patterned to form the bottom electrode 108 utilizing a suitable sputter deposition tool and a suitable etching tool. During deposition and patterning, traces may also be formed for electrical contact between the cantilevers 106 and external electronics.

The method further includes forming the first piezoelectric sensing unit 110, which may be accomplished by blanket deposition of a piezoelectric material on the bottom electrode 108. For example, a blanket AlN layer (from about 1.5 to 2.5 µm thick) may be deposited on the bottom electrode 108 utilizing an AMS 2004 AlN sputter tool to achieve a stress passivated AlN layer on the bottom electrode 108.

The method further includes forming the middle electrode 112 on the first piezoelectric sensing unit 110. In an example, the middle electrode 112 is formed by depositing and patterning a Ti/Pt layer on the first piezoelectric sensing unit 110. Additionally, traces may be formed during the deposition and patterning for electrical connection to the amplifier 122.

The method further includes forming the second piezoelectric sensing unit 114 on the middle electrode 112. This may be accomplished, for example, by blanket deposition of another piezoelectric material on the middle electrode 112. For example, a blanket AlN layer (with a thickness of from 1.5 to 2.5 µm) may be deposited on the middle electrode 112 utilizing a suitable sputter deposition tool, such as an AMS 2004 AlN sputter tool with a focus on achieving a stress passivated AlN layer.

Figure 9B:
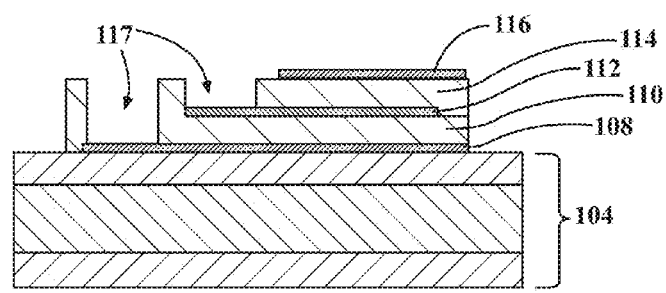

Referring now to FIG. 9B, the method includes forming vias 117 for accessing the bottom 108, middle 112, and top 116 electrodes. The vias may be formed by cutting through the piezoelectric sensing units 110, 114 to access the electrical traces formed in the middle 112 and bottom 108 electrodes. For example, a blanket layer of about 2 µm thick of PECVD oxide may be deposited on the second piezoelectric sensing unit 114 followed by a SPR 220 patterned photoresist layer defining the via locations. An oxide etch may be used to pattern the via shape into the PECVD oxide layer, followed by a Cl-based RIE etch to etch the via into the piezoelectric sensing units 110, 114. The etching is terminated within 1 µm of the electrode depth for each of the middle 112 and bottom 108 electrodes, as the RIE etch does not have the sensitivity to stop directly on the electrode 108, 112. The photoresist may be removed, and the patterned oxide serves as the masking layer for removal of the remaining piezoelectric material of the piezoelectric sensing units 110, 114 and stopping at the underlying electrode 108, 112. The oxide layer is then removed (with the photoresist protecting the opened vias) using an HF bath.

After etching, the method includes forming the top electrode 116 by deposition and patterning of a blanket metal on the second piezoelectric sensing unit 114. In an example, the top electrode 116 is formed by depositing and patterning a Ti/Pt layer on the second piezoelectric sensing unit 114. In this step, the vias 117 may be protected during patterning of the Ti/Pt layer to prevent overetching of the Ti/Pt layer.

In an example, the method further includes thinning the block 104 so that the device 100 suitably fits into the cochlea. In instances where a silicon wafer is used, thinning may be accomplished, for example, by grinding, chemical mechanical polishing (CMP), and/or deep reactive-ion etching (DRIE). The thinning process can be performed at any stage of the fabrication process, depending on how the fabrication process is organized. Alternatively, a silicon-on-insulator (SOI) wafer can be thinned by utilizing a wet-etch to release the thinner oxide layer from the backside of the wafer.

A blanket layer of AlN may then be patterned to define the shapes of the cantilevers 106. Because AlN acts as an insulator, the blanket AlN layer may be left along the full length of the probe 102 and traces are run in the bottom electrode layer 108 for electrical insulation. In an example, a Cr/Au layer (about 20 to 400 µm thick) may be formed for additional electrical connections, including bond pads and shorting between the top 116 and bottom 108 electrodes.

Figure 8A:
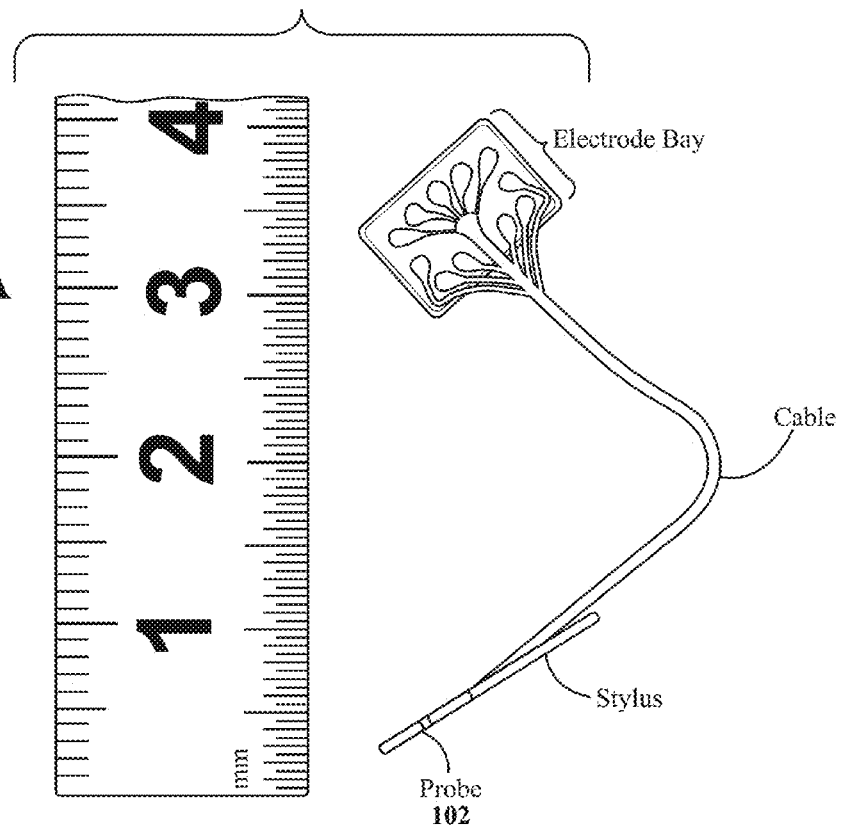
FIG. 8A illustrates an implantable cochlear implant having a probe with a silicon backbone and an array of five piezoelectric cantilevers, an electrode bay with electrodes for monitoring, and a ribbon cable to connect the probe with the electrode bay. The cochlear implant further has a breakoff or removable stylus which may be used to facilitate implantation of the cochlear implant.
Figure 8B:
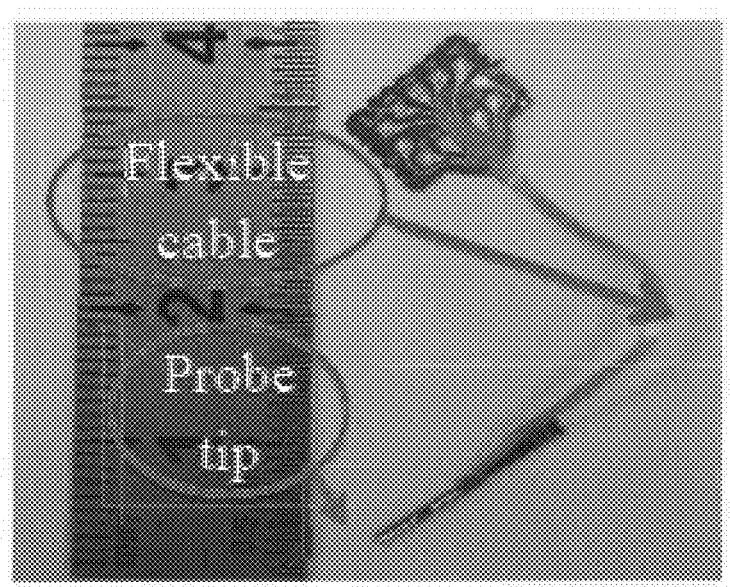
FIG. 8B is a photograph of the implantable cochlear implant illustrated in FIG. 8A.
Figure 9C:
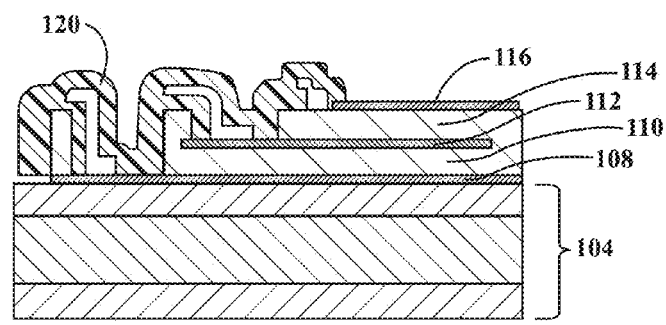
Figure 9D:
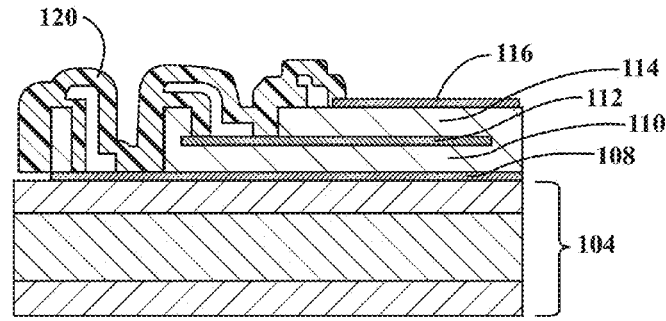

Additional methods steps may be performed to obtain a desired shape of the device 100, flexibility, and degree of external monitoring capability. With reference to FIG. 9D, the device 100 shape may be defined by patterning the substrate to form a desired bulk material shape that forms the backbone of the probe 102 and the cantilevers 106 utilizing deep reactive-ion etching (DRIE) or wet etching technique. Typically, the backbone of the probe 102 may be shaped into a shank that holds or supports a number of cantilevers 106 (a non-flexible probe), or may be shaped into a series of blocks that are held together by the compliant element 118 and communication line 120 (flexible probe) as shown in FIGS. 8A and 8B. The patterning process may also be used to form an electrode bay to house contact pads for electrical monitoring and a break-away stylus to assist with insertion of the probe 102 into the cochlea.

External monitoring and amplification may be built by building a ribbon cable (such as a cable comprising Parylene C/Cr and Au/Parylene C). With reference to FIG. 9C, this method includes depositing a blanket insulating material (such as Parylene C) to form the flexible polymer and then patterning using photolithography to form an underside of the cable. The method further includes patterning a metal on the insulating material to form metal traces for electrical connections. Further, the method includes depositing and patterning a second insulating material on the metal to form an upper layer of the cable. The ribbon cable may be used to connect the probe 102 to an external electrical bay (as shown in FIG. 8), as the communication line 120 for electrical connection between separate cantilevers 106, and/or for adding levels of traces along the probe 102 that are electrically isolated. In an embodiment, the traces may be used to connect the probe 102 to power and/or an external wireless connection.

In an embodiment, the communication line 120 may be formed by forming a first polymer layer and forming a layer of patterned metal on the polymer layer. The step of forming may be accomplished by blanket deposition of a metal and selectively etching the metal utilizing a wet or dry RIE etching process. Alternatively, the step of forming may be accomplished by deposition of the metal utilizing a liftoff process. The liftoff process includes depositing the metal on top of a patterned layer of photoresist, and washing off the photoresist (with the metal attached to the photoresist) with acetone. After washing off, the metal deposited on the exposed areas of the polymer layer remain. The communication line 120 is further formed by forming a second polymer layer on the patterned material layer.

For flexible devices (such as the device 100), another method may be used to build a mass-spring system that is curved and can be deformed and/or be compressed into a straight shape. This method involves defining the shape of the meander spring using a photoresist and forming a metal connect between each block 104 by electroplating. The metal connect is flexible enough to allow lateral bending, but is stiff enough to prevent the metal connect from being under the weight of gravity. Alternatively, the method may involve defining the blocks 104 utilizing a DRIE process, and then spinning or injecting a polymer into a defined trench to form the flexible compliant element 118 between the blocks 104.

Several embodiments of the device 100 which is a fully implantable cochlear implant have been described above. In each of these embodiments, the device 100 utilizes piezoelectric cantilevers 106 separated by the compliant element 118. As previously described, the piezoelectric cantilevers 106 include at least one piezoelectric sensing unit 110, 114 that convert vibrations into electrical signals to stimulate the auditory nerves without having to use an external sound processing unit. Additionally, the compliant element 118 provides flexibility to the device 100 in the plane of curvature of the cochlear and provides stiffness out of the plane of curvature of the cochlea. The communication line 120, which separates the cantilevers 106, also provides stiffness to the device 100 in the plane of curvature of the cochlea.

Figure 10:
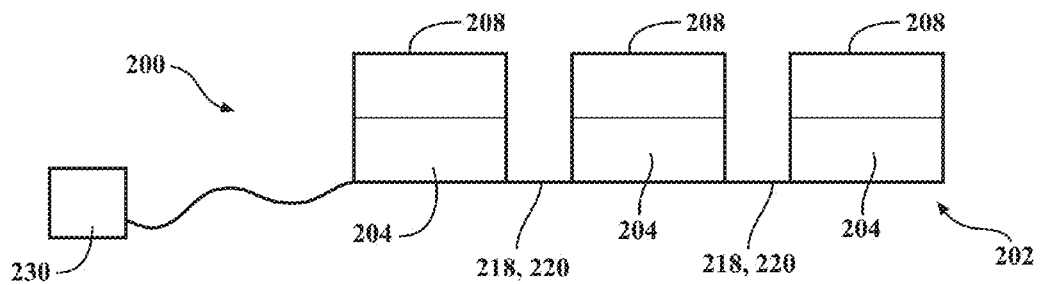
FIG. 10 schematically illustrates a side view of another embodiment of a device to be implanted into the scala tympani of the cochlea.

Another embodiment of the device 200 is shown in FIG. 10. Similar to the traditional cochlear implant, the device 200 comprises a probe 202 with a plurality of blocks 204 and electrodes 208 deposited on the blocks 204. Since the device 200 does not have piezoelectric sensing units. However, the device 200 has a processing unit 230 external to the cochlea for processing sound into an electrical signal. It is to be understood that while the processing unit 230 is external to the cochlea, the processing unit 230 is still internal to the human's head. Accordingly, the device 200 is still considered to be fully implantable. The electrodes 208 transmit the electrical signal to the auditory nerve. The device 200 also comprises a compliant element 218 disposed between adjacent blocks 204, and the compliant element 218 may be a meander spring or a combination of a meander spring and a flexible polymer. Additionally, the device 200 includes a communication line 220. The compliant element 218 and the communication line 220 are the same as the compliant element 118 and communication line 120 that were previously described. While the device 200 utilizes external processing, the device 200 exhibits the flexibility in the plane of curvature of the cochlea and stiffness out of the plane of curvature of the cochlea. Accordingly, the probe 202 can be easily implanted into the scala tympani of the cochlea similar to the device 100 described above.

The device 200 may be fabricated utilizing the same fabrication method described above for fabricating the device 100, except for the steps that involve forming the piezoelectric cantilevers.

The devices 100, 200 described above advantageously have a lower power consumption compared to traditional or other known cochlear implants, has a higher degree of control over the geometry of the probe 102, 202. The device 100, 200 is also smaller compared to other known cochlear implants. Further, lower latency is evident with the device 100 which is fully implantable, because sensing is accomplished in the scala tympani of the cochlea rather than by external microphones.

The invention has been described in an illustrative manner, and it is to be understood that the terminology which has been used is intended to be in the nature of words of description rather than of limitation. It is now apparent to those skilled in the art that many modifications and variations of the present invention are possible in light of the above teachings. It is, therefore, to be understood that the invention may be practiced otherwise than as specifically described.

What is claimed is:

1. A device for implantation into a scalia tympani of a cochlea that is connected to an auditory nerve with the cochlea having a plane of curvature and including a cochlear fluid, said device comprising:
    a plurality of blocks;
    a plurality of compliant elements interconnecting said plurality of blocks for imparting flexibility to said device in the plane of curvature of the cochlea and for imparting stiffness to said device out of the plane of curvature of the cochlea;
    a plurality of piezoelectric elements with at least one of said plurality of piezoelectric elements disposed on said blocks with each of said plurality of piezoelectric elements comprising:
        at least one piezoelectric sensing unit for sensing vibration of the cochlear fluid inside the cochlea and for converting the vibration into an electrical signal; and
        at least one electrode for transmitting the electrical signal to the auditory nerve; and
    a plurality of communication lines for transmitting the electrical signal through said device with one of said plurality of communication lines disposed between each of said pair of adjacent blocks and adjacent said compliant element.

2. The device as set forth in claim 1 wherein each of said plurality of compliant elements is chosen from a meander spring and a combination of a meander spring and a flexible polymer.

3. The device as set forth in claim 2 wherein each of said plurality of compliant elements is the combination of the meander spring and the flexible polymer, and wherein the flexible polymer surrounds the meander spring.

4. The device as set forth in claim 1 wherein each of said plurality of compliant elements is disposed between adjacent blocks of said plurality of blocks.

5. The device as set forth in claim 1 wherein each of said plurality of piezoelectric elements has a length of from 80 to 120 μm.

6. The device as set forth in claim 1 wherein each of said plurality of piezoelectric elements has a one of a fixed-free configuration or a fixed-fixed configuration.

7. The device as set forth in claim 1 further comprising an amplifier coupled to at least one of said plurality of blocks for amplifying the electrical signal.

8. The device as set forth in claim 1 wherein said device has a length and said at least one piezoelectric sensing unit has a width of from 300 to 500 μm and a length of from 200 to 300 μm.

9. The device as set forth in claim 8 wherein said plurality of piezoelectric elements individually have a length, and said length of a first one of said plurality of piezoelectric elements is different from said length of a second one of said plurality of piezoelectric elements.

10. The device as set forth in claim 1 wherein said at least one piezoelectric sensing unit includes a first and a second piezoelectric sensing unit and said at least one electrode comprises a top, bottom, and middle electrode, with said first piezoelectric sensing unit disposed on said bottom electrode, said middle electrode disposed on said first piezoelectric sensing unit, said second piezoelectric sensing unit disposed on said middle electrode, and said top electrode disposed on said second piezoelectric sensing unit.

11. The device as set forth in claim 1 wherein said plurality of blocks is sequentially arranged.

12. The device as set forth in claim 1 wherein each of said plurality of blocks comprises a material chosen from silicon, silicon oxides, silicones, polyimides, and combinations thereof.

13. The device as set forth in claim 1 wherein each of said plurality of communication lines is chosen from a wire, a series of wires, a cable, and combinations thereof.

14. The device as set forth in claim 1 wherein one of said plurality of blocks is an anchor of said device for at least one of communicating with, testing, and powering said device.

15. The device as set forth in claim 1 wherein said device is completely implantable in the cochlea.

* * * * *